April 30, 1963 E. E. WILLIAMS Plant Pat. 2,254
APRICOT TREE
Filed Oct. 27, 1960
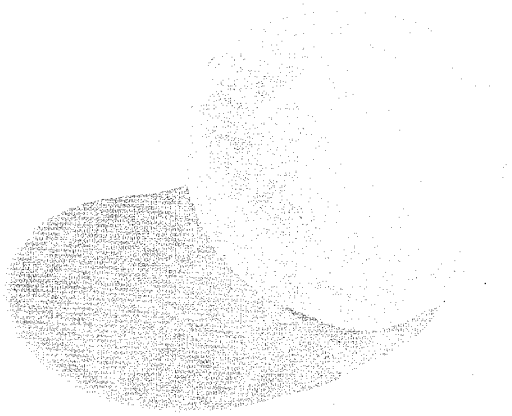

United States Patent Office

Plant Pat. 2,254
Patented Apr. 30, 1963

2,254
APRICOT TREE

Edgar E. Williams, Trinidad, Wash., assignor to Pacific Coast Nursery, Portland, Oreg., a firm doing business as a partnership Filed Oct. 27, 1960, Ser. No. 65,545
1 Claim. (Cl. 47—62)

The present invention relates to a new and distinct variety of apricot tree originated as a sport of the variety known as Moorpark (unpatented). The new variety was discovered by me in 1945 in a cultivated orchard on my property in Trinidad, Washington.

The parent variety Moorpark is characterized by branches that spread laterally. The leaves have a tapering point and are finely serrated.

The new variety is substantially identical in all respects with the aforementioned parent, except that the skin of the fruit of the new variety is characterized by a mottled blush and the fruit ripens about three weeks earlier than its parent Moorpak in and adjacent Wentachee, Washington.

Asexual reproduction of the new variety by grafting and budding in the Columbia River Basin in and adjacent Chelan County, Washington, establishes that the foregoing characteristics run true to form and are fixed and are transmitted through succeeding propagations.

The accompanying drawing shows a specimen of the fruit, in elevation.

The following is a detailed description of the new variety based upon observations of specimens grown in and adjacent Trinidad, Washington in the Columbia River Valley adjacent Chelan County, with color terminology in accordance with Nickerson Color Fan by Munsell Color Company as indicated, except where the general color terms of ordinary dictionary significance are obvious:

Dates of first picking: June 15 as compared to July 3, of parent stock.

Tree: Fairly large, vigorous, spreading, hardy, productive, regular bearing.

*Branches.*—Laterally spreading.

*Leaves.*—Distinctive with a tapering point which is finely serrated and the color is slightly darker than color 7.5CY 4/4.

Flowers: The blossom date is the same as the parent Moorpark.

Fruit: Moderately firm; 2 inches to 2⅜ inches in diameter; ovate; halves substantially equal with well defined suture; stem cavity is medium and pit cavity is medium to large. Color—Coloration is similar to Moorpark but it presents a mottled red blush at greatest exposure to sunlight and which diffuses in diminishing brightness over one-half of the fruit.

Flesh: Firm.

Use: Market and dessert.

Keeping quality: Medium.

I claim:

A new and distinct variety of apricot tree substantially as shown and described characterized as to novelty by its similarity to its parent variety (Moorpark) but distinguished therefrom by a diffused mottled blush over approximately one-half of the surface and having a harvest date approximately three weeks earlier than its parent variety.

No references cited.